United States Patent [19]

Hooper

[11] Patent Number: 4,488,927
[45] Date of Patent: Dec. 18, 1984

[54] APPARATUS FOR C-FOLDING A COVERING WEB ABOUT A LONGITUDINALLY FLEXIBLE ARTICLE

[75] Inventor: Leonard C. Hooper, Cincinnati, Ohio

[73] Assignee: The Procter & Gamble Company, Cincinnati, Ohio

[21] Appl. No.: 494,842

[22] Filed: May 16, 1983

[51] Int. Cl.³ .............................................. B31F 1/00
[52] U.S. Cl. .................................. 156/464; 156/465; 156/468; 156/202; 156/204
[58] Field of Search ............... 156/199, 200, 202, 204, 156/461, 463, 465, 467, 468, 464, 459, 443, 535, 543; 220/5, 16, 41

[56] References Cited

U.S. PATENT DOCUMENTS

| | | | |
|---|---|---|---|
| 2,283,137 | 5/1942 | Fine | 156/202 |
| 3,143,456 | 8/1964 | McGrath et al. | 156/202 |
| 3,313,672 | 4/1967 | Covino | 156/467 |
| 3,730,798 | 5/1973 | Franz | 156/464 |
| 3,859,161 | 1/1975 | McLeod | 156/202 |

Primary Examiner—Edward Kimlin
Assistant Examiner—Merrell Cashion
Attorney, Agent, or Firm—Thomas J. Slone; Fredrick H. Braun; Richard C. Witte

[57] ABSTRACT

An apparatus for C-folding a running length of a covering web such as a polyethylene ribbon about a longitudinally flexible article such as a running length of a core web for making disposable diapers or a stream of longitudinally spaced discrete core segments of such a core web; i.e., a stream of absorbent cores for disposable diapers. The apparatus effects folding each longitudinal edge portion of a covering web downwardly and inwardly about an adjacent longitudinal edge region of the article as the web and the article are forwarded through the apparatus. Each longitudinal edge portion is so folded intermediate a transverse turning member which it passes under, and an oblique turning edge disposed downstream therefrom and over which it passes; and the longitudinal edge portions of the running web and the adjacent longitudinal edge regions of the article become juxtaposed upon passing over their respective oblique folding edges. This is effected without the surfaces of the edge portions of the covering web being contacted by other members of the apparatus; and without unevenly straining the covering web. Preferably the apparatus also gravitationally applies a longitudinally extending bead of a suitable adhesive on the inner surface of each longitudinal edge portion so that adjacent edge portions and edge regions become adhesively secured together upon being juxtaposed.

7 Claims, 8 Drawing Figures

APPARATUS FOR C-FOLDING A COVERING WEB ABOUT A LONGITUDINALLY FLEXIBLE ARTICLE

DESCRIPTION

Technical Field

This invention pertains to apparatus for at least partially wrapping a running length of one web about a flexible article such as a running length of a core web or stream of segments thereof, and for securing longitudinal edge portions of the one web to juxtaposed longitudinal edge regions of the article: for example, C-folding a running length of backsheet material (e.g., polyethylene film) for diposable diapers about a running length of absorbent core material bonded to a topsheet web (e.g., nonwoven polypropylene) to produce, when so secured together and segmented, a stream of discrete disposable diapers.

Background Art

Issued patents disclose apparatus for C-folding a running length of a covering web about an article or another web or a stream of articles on-the-fly; and for adhesively securing longitudinal edge portions of the covering web to longitudinal edge regions of the covered article, articles, or web. Representative U.S. Pat. Nos. which effect this along linear paths include 3,020,599 which issued Feb. 13, 1962 to P. H. Pukis et al; 3,356,092 which issued Dec. 5, 1967 to C. G. Joa; 3,366,155 which issued Jan. 30, 1968 to J. F. Champaigne, Jr.; 3,547,930 which issued Dec. 15, 1970 to N. V. Blomquist et al; and 3,669,800 which issued June 13, 1972 to G. T. Gore. Necessarily, however, each of these unevenly longitudinally strains the covering web inasmuch as the edge portions must traverse greater distances than the central portions of the covering web. Such uneven strains precipitate, upon relaxation, such undesirable product attributes as wrinkled covers.

U.S. Pat. No. 3,730,798 which issued May 1, 1973 to N. J. Franz discloses a non-linear apparatus in which a covering web is C-folded as it traverses a folding board having a complex angular shape with U-shape channels along side portions thereof. Indeed, the longitudinal edge portions of the covering web are reverse folded as they are drawn through the U-shape channels of the folding board in contacting relation therewith. The large sliding surface areas and the plurality of edges over which the web is drawn precipitate substantial friction and drag on the web which, especially with respect to webs having elasticized portions, induce wrinkling and/or other distortions and/or other deleterious ramifications. The present invention overcomes these drag and distortion problems.

DISCLOSURE OF THE INVENTION

In accordance with one aspect of the present invention, an apparatus is provided for longitudinally C-folding or C-wrapping a running length of a flexible covering web about an article and for adhesively securing longitudinal edge portions of the covering web to juxtaposed longitudinal edge regions of the bottom surface of the article. The apparatus comprises means for doing this without unevenly straining the covering web and without reverse folding the longitudinal edge portions thereof. Such means may comprise a transverse turning member such as a roll, a first planar folding board having an upstream end disposed subjacent the turning member, a second planar folding board immediately downstream from said first folding board and pitched downwardly therefrom at a predetermined pitch angle, means for forwarding the article onto said first folding board, and means for forwarding the covering web onto and about the turning member in a flat-out state so that its central span becomes juxtaposed the top surface of the article. The first folding board has a nominal width equal to or greater than the width of the article and has longitudinally extending side edges. Equal widths are preferred for tightly wrapped article edges, and wider folding boards provide marginal edges of covering web which extend beyond the edges of the article. The second folding board has an oblique folding edge at each upstream corner, and the oblique folding edges are canted upstream at a predetermined acute angle with respect to the longitudinal centerline of the second folding board. The apparatus further comprises means for forwarding the web and the article together through the apparatus so that the unsupported longitudinal edge portions of the covering web which are disposed outwardly from the longitudinal side edges of the first folding board are gradually U-folded downwardly and inwardly intermediate the turning member and the oblique folding edges; and so that the longitudinal edge portions of the covering web become juxtaposed the longitudinal edge regions of the bottom surface of the article only upon passing over the oblique folding edges of the second folding board. The predetermined pitch angle is so related to the predetermined acute angle and the folding boards are so sized and configured that all portions of the covering web traverse the same distance. The apparatus may further include means for gravitationally applying a bead of adhesive to the ultimate inside surface of each longitudinal edge portion of the covering web to effect adhesive securement upon their becoming juxtaposed the longitudinal edge regions of the bottom surface of the article; means for elasticizing the longitudinal edge portions of the covering web; and means for receiving and forwarding the article in the form of a running length of a core web.

BRIEF DESCRIPTIONS OF THE DRAWINGS

While the specification concludes with claims particularly pointing out and distinctly claiming the subject matter regarded as forming the present invention, it is believed the invention will be better understood from the following descriptions taken in conjunction with the accompanying drawings in which the same features are identically designated in the several views, and in which the thickness of the covering web designated 38 is exaggerated for clarity, and:

Figure 3:
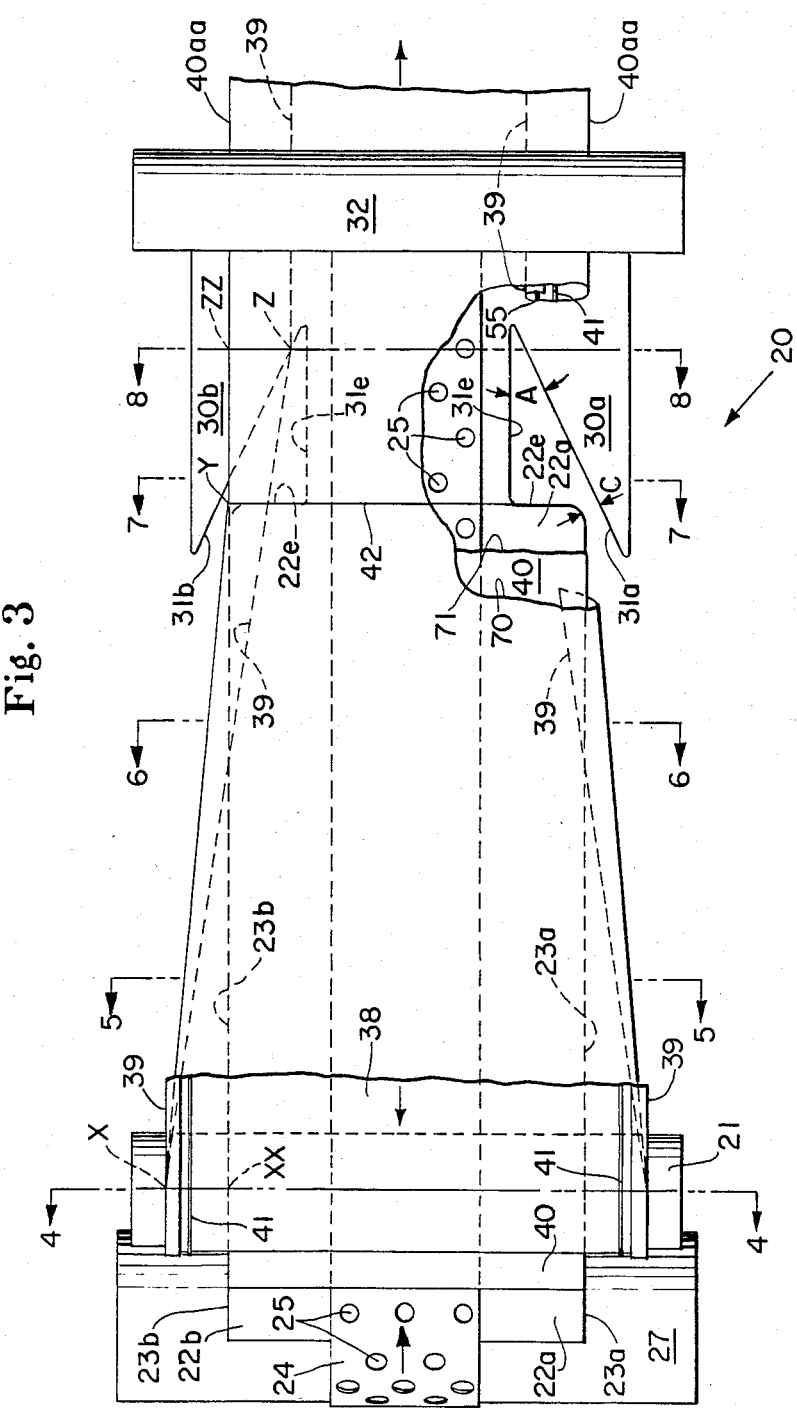
FIG. 3 is a fragmentary top view of the apparatus shown in FIG. 1.

FIGS. 4 through 8 are enlarged scale, fragmentary sectional views taken along section lines 4—4 through 8—8, respectively, on FIG. 3, and looking upstream in the apparatus.

DETAILED DESCRIPTION OF THE INVENTION

Figure 1:
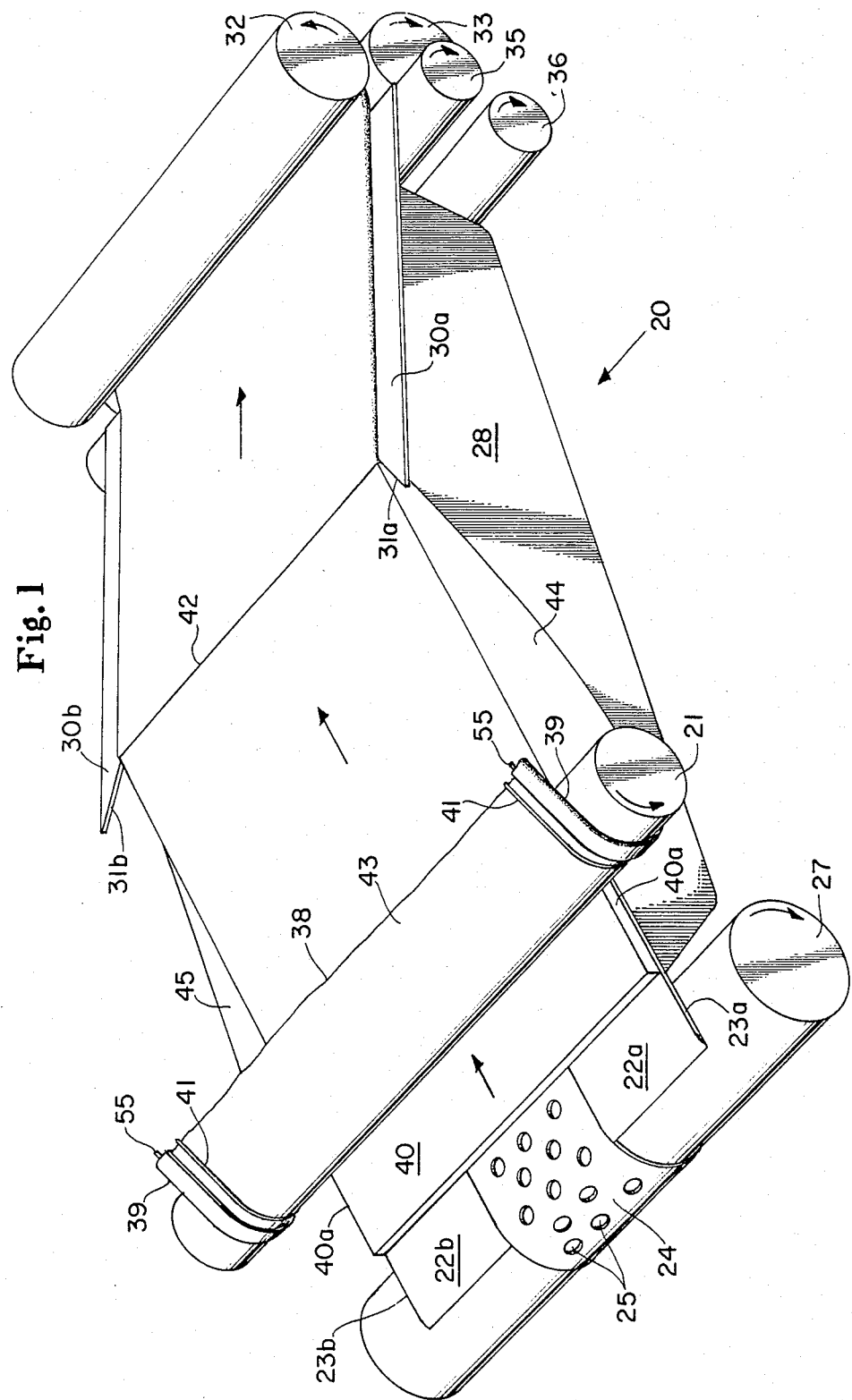
FIG. 1 is a fragmentary perspective view of an exemplary apparatus embodiment of the present invention.

A fragmentary portion of an exemplary apparatus 20 embodying the present invention is shown in perspective in FIG. 1 to include a turning roll 21; a first planar folding board comprising a right half 22a having a longitudinal side edge 23a, and a left half 22b having a longitudinal side edge 23b; a conveyor belt 24 having a plurality of apertures 25; a conveyor guide roll 27; a vacuum box 28; a second planar folding board comprising a right half 30a having an oblique folding edge 31a, and a left half 30b having an oblique folding edge 31b; drive-nip rolls 32 and 33; and conveyor return rolls 35 and 36. Also, FIG. 1 includes fragmentary portions of a covering web 38 having side edges 39 and inner surface 43; and an article 40 having side edges 40a. The longitudinal edge portions of the covering web disposed outboard of the longitudinal side edges 23a and 23b of the first folding board halves 22a and 22b, respectively, are designated 44 and 45, respectively, and each is provided with a longitudinal glue bead 41 by applicators disposed upstream but not shown in FIG. 1. The apparatus further comprises a frame, drive means for conveyor belt 24 and drive-nip rolls 32 and 33, and means for maintaining a predetermined level of vacuum in vacuum box 28, which elements are not shown in FIG. 1 to avoid obfuscating the essence of the present invention.

While apparatus 20, FIG. 1, is capable of C-folding a covering web about an article 40, or a stream of such articles which may or may not be longitudinally spaced, or a running length of an article such as a core web for making disposable diapers, the following description primarily refers in the singular to an article for simplicity of description rather than intending to thereby limit the present invention. Moreover, in the event the article to be C-wrapped is such a continuous web, the conveyor belt 24 and its ancillary guide rolls 27, 35, and 36 as well as vacuum box 28 may be removed or disabled inasmuch as the driven nip-rolls 32 and 33 would then be able to draw both webs 38 and 40 through the apparatus.

Briefly, an article 40 is received on the perforated belt 24 and then forwarded through the apparatus on conveyor belt 24 by applying vacuum from box 28 through a slotted top wall of box 28 and through the apertures 25 in belt 24. Concomitantly, the covering web 38 is drawn through the apparatus by driving the nip rolls 32 and 33 at a predetermined velocity. Covering web 38 passes about turning roll 21 in a flat-out state whereupon its longitudinally extending central portion becomes juxtaposed the top surface of article 40. The covering web 38 and the article 40 are then forwarded together over the upwardly inclined first folding board, and over the downwardly sloped second folding board and in so doing they pass the break line between the two folding boards which break line is designated 42 in FIG. 1. Importantly, article 40 must necessarily be sufficiently longitudinally flexible to follow the folding boards as it passes over break line 42. Concomitantly, the longitudinal edge portions of the covering web are progressively folded downwardly and inwardly by virtue of their being threaded upwardly over the oblique folding edges 31a and 31b. This effects C-folding the covering web so that its longitudinal edge portions become juxtaposed and adhesively secured to the longitudinal edge regions of the bottom surface of article 40 only upon passing over folding edges 31a and 31b. Thus, the surfaces of the longitudinal edge portions of the covering web 38 which extend between the line of contact XT, FIG. 2, with turning roll 21 and the folding edges 31a and 31b are not contacted by any other members of the apparatus. Also, no part of either longitudinal edge portion 44 or 45 of the covering web is reverse folded; that is, first folded one way and then another as is the case for example with the longitudinal edge portions of web 31 in the hereinbefore referenced U.S. Pat. No. 3,730,798 wherein the edges are first folded UP (FIG. 6); are then formed into outwardly facing U-shapes (FIG. 9); and ultimately become inwardly facing U-shapes (FIG. 10). Additionally, the longitudinally edge portions 44 and 45 do not slide across any machine member disposed upstream of the oblique folding edges 31a and 31b in the exemplary apparatus illustrated in the several figures.

Figure 2:
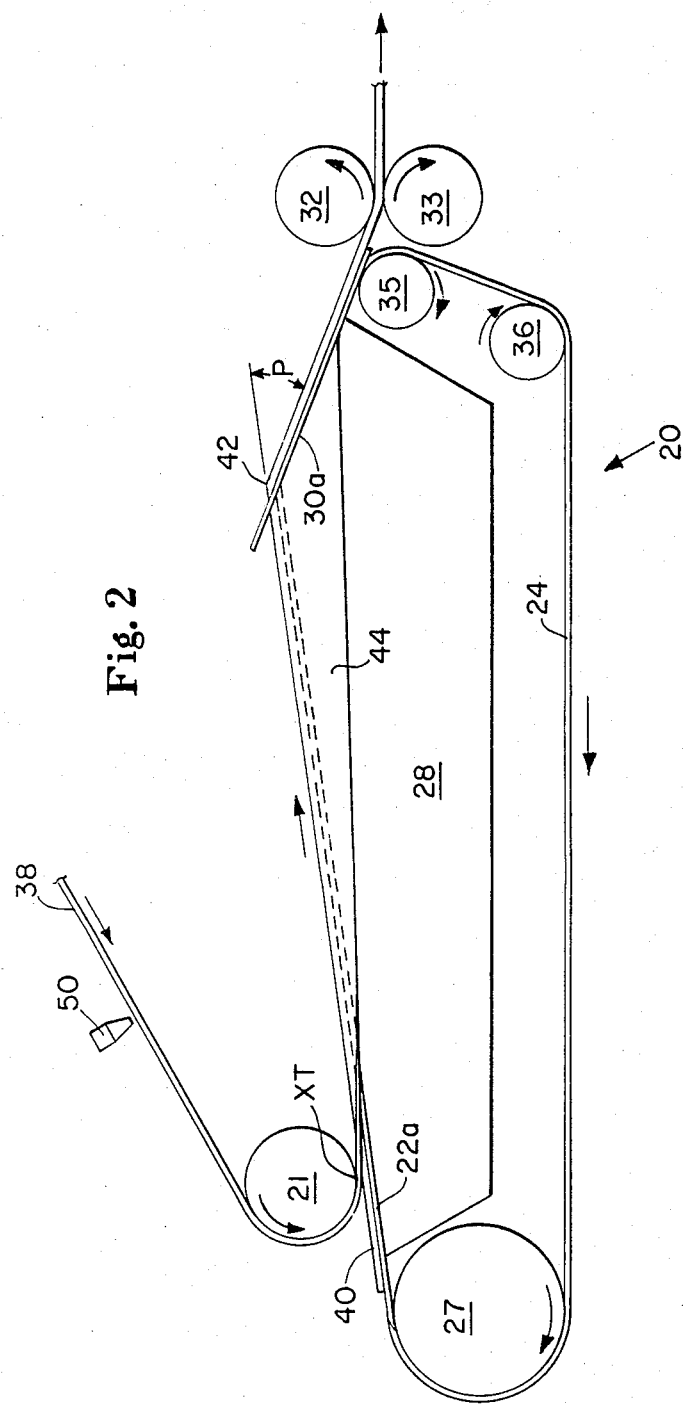
FIG. 2 is a fragmentary side elevational view of the apparatus shown in FIG. 1.

Referring now to FIGS. 2 and 3, they are side elevational and top views, respectively, of the apparatus 20, FIG. 1, and all of the features thereof are identically designated in the several views.

Apparatus 20, FIG. 2, also includes an adhesive applicator 50 for applying the adhesive beads designated 41, FIG. 1. FIG. 2 further shows that planar folding board half 30a is pitched downwardly with respect to planar folding board half 22a at a pitch angle P. In the exemplary apparatus shown, P has a nominal value of thirty (30) degrees. XT in FIG. 2 is the transverse line of tangency between web 38 and turning roll 21. Additionally, FIG. 2 shows wrapped article issuing from between nip rolls 32 and 33. Means not shown are provided for biasing nip rolls 32 and 33 together so that they will function to calender wrapped articles to a controlled extent, and will function to continuously draw the web 38 through the apparatus regardless of intervening longitudinal spaces between successive articles 40.

The first folding board comprising right half 22a and left half 22b may be a unitary assembly in which the halves are laterally spaced by a perforated or slotted central span which, in turn, would in fact function as the top wall of vacuum box 28, FIGS. 1 and 2, and which underlies the perforated conveyor belt 24. However, whether the halves 22a and 22b are or are not integrated into a unitary assembly, they are coplanar and have aligned trailing edges 22e which define break line 42. Additionally, as stated above, halves 22a and 22b have longitudinal outboard side edges 23a and 23b, respectively. Also, the outboard corners of halves 22a and 22b are radiused and spaced from the adjacent oblique folding edges 31a and 31b, respectively, to provide a clearance therebetween designated C in FIG. 3. As will be described more fully hereinafter in conjunction with describing FIGS. 4 through 8, the common plane of the top surfaces of halves 22a and 22b also includes the top surface of the portion of conveyor belt 24 disposed therebetween.

In FIG. 3, a portion of covering web 38 is torn away along tear line 70, and a portion of article 40 is torn away along tear line 71 in order to reveal the underlying structure of apparatus 20. Also, the outer edges of the wrapped article 40 are designated 40aa whereas the longitudinal edges of article 40 are designated 40a.

Still referring to FIG. 3, the second folding board comprising halves 30a and 30b may also be integrated into a unitary assembly as described above with respect to the first folding board, or by discrete halves disposed outboard of the conveyor belt 24. In either configuration, the top surfaces of halves 30a and 30b are coplanar with top surface of the portion of conveyor belt 24 disposed therebetween. Each of halves 30a and 30b are configured to have a V-shape notch which faces upstream and which has an acute angle A between its edge 31e and its oblique folding edge, namely oblique folding edges 31a and 31b, respectively. These notches constitute preferred means for the longitudinal edge portions of covering web 38 to pass from under the trailing edge segments 22e of the first folding board halves 22a and 22b and thence over the oblique folding edges as the web is drawn through the apparatus.

Oblique folding edges 31a and 31b, FIG. 3, may be radiused to facilitate sliding the longitudinal edge portions of covering web thereacross. Preferably, however, round rods may be secured to those edges to provide such radii rather than machine radii on the edges of the planar folding board halves. For example, rods having nominal diameters of about one-half centimeter have been secured to flat edges of half-centimeter thick folding boards and have been found to be very satisfactory in operation.

Acute angle A, FIG. 3, is so related to pitch angle P referred to above that, for a given length between XT and the break line (i.e., edges 22e), every portion of the covering web 38 nominally traverses substantially the same path length. That is, angle A is so related to angle P that the diagonal path length of edge 39 of web 38 intermediate point X and Z is equal to the sum of the machine-direction path segments which extend between points XX and Y, and Y to ZZ. Points X and XX lie in the tangent line XT, FIG. 2; point Y is an outboard downstream corner of folding board half 22b; and points Z and ZZ lie in the top surface of folding board half 30b along section line 8—8. Also, point Z is the point on oblique folding edge 31b over which edge 39 of web 38 is drawn. Additionally, angles A and P, and the shapes of oblique folding edges 31a and 31b may have to be adjusted somewhat through trial and error to compensate the geometry of the apparatus for the various thicknesses of articles to be C-wrapped. However, in an exemplary embodiment of apparatus 20 which is used to C-fold a running length of polyethylene about a stream of longitudinally spaced discrete cores of disposable diapers which have previously been combined with suitable topsheets, angles A and P have nominal values of twenty-five (25) degrees and thirty (30) degrees, respectively, and the distance between tangent line XT and the break line (i.e., edges 22e) is about forty (40) centimeters. The resulting disposable diapers have elasticized cuffs due to the strands of elastic 55 being disposed inwardly as shown in FIG. 3 from the glue beads 41 which secure the longitudinal edge portions of the backsheet (i.e., the covering web 38) to bottom surface regions of the cores (i.e., articles 40) shown in FIG. 3, and in FIG. 8 which is discussed below.

Referring now to FIGS. 4 through 8 inclusive, they are sequential fragmentary sectional views taken along section lines 4—4 through 8—8, respectively, in FIG. 3, and looking in the upstream direction. Briefly, they manifest the progressive downward and inward folding of the longitudinal edge portions of the covering web 38 without their being reverse folded and without their being contacted by physical members of the apparatus prior to passing up and over the oblique folding edges as described above and as shown in FIG. 3. Additionally, it is apparent from FIGS. 7 and 8 that the distal edge regions of the longitudinal edge portions of web 38 which are disposed between side edges 39 and glue beads 41 are elasticized by elastic 55 which is secured in a stretched state in side edge hems of web 38, only one of which hems is shown in the fragmentary sectional views, FIGS. 4 through 8; and that those distal edge regions are not adhesively secured to article 40. Thus, this construction provides disposable diapers with elasticized cuffs which are free to be spaced from the side edges of the diaper core when the diaper is applied to an infant or other user.

Figure 4:
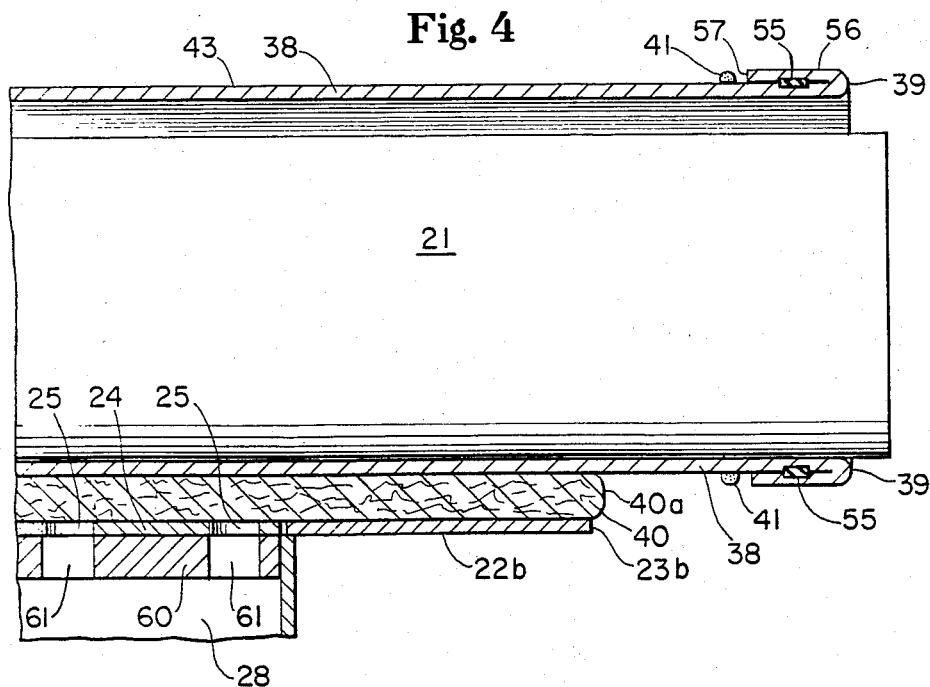
Figure 5:
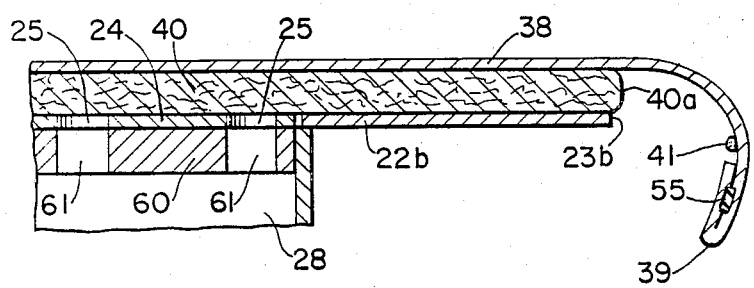
Figure 6:
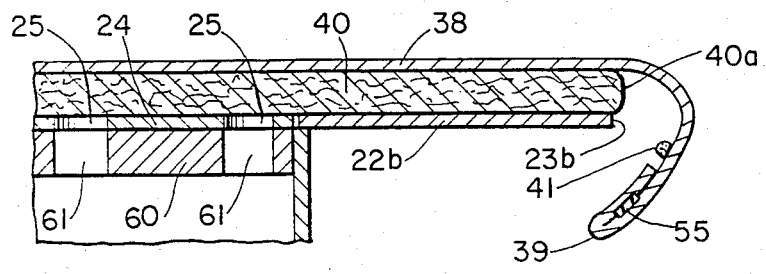
Figure 7:
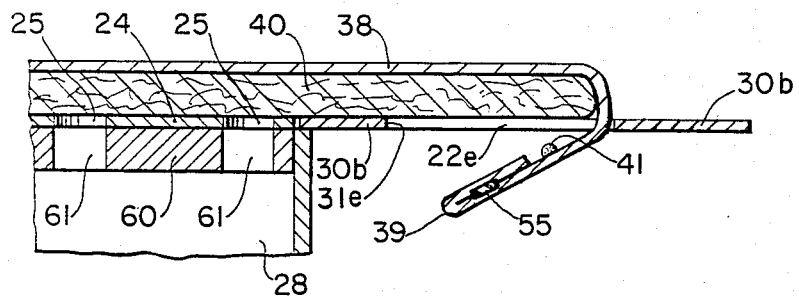
Figure 8:
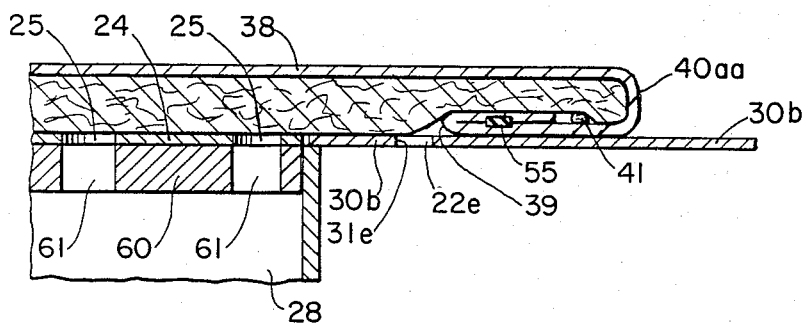

Referring now to FIG. 4 specifically, the above described coplanar relationship of the top surfaces of conveyor belt 24 and the halves of the first folding board is apparent albeit only folding board half 22b is shown in the fragmentary view. Additionally, FIG. 4 also shows the top wall 60 of vacuum box 28 to be comprised of a plurality of transversely spaced longerons to provide slots 61 through the top wall which are sized and configured with respect to the apertures 25 through conveyor belt 24 to enable vacuum in box 28 to be applied to the bottom surface of article 40 disposed thereabove. Thus the movement of conveyor belt 24 by drive means not shown will cause the article 40 to be forwarded as also described above. These construction features are repeated and identically designated in FIGS. 5 through 8 to further facilitate understanding of the present invention.

As described above, apparatus 20 comprises means for practicing the method of C-folding a covering web about an article, or stream of articles, or a continuous running-length article which method comprises the steps of forwarding the article and the longitudinal central portion of the covering web in juxtaposed relation along first and second linear paths which are related to each other by a predetermined pitch angle along a break line, commencing folding the longitudinal edge portions of the covering web upstream of the break line, and drawing the longitudinal edge portions of the covering web over oblique folding edges which are in the plane of the second linear path immediately downstream from the break line and so disposed at a predetermined acute angle with respect to the second linear path that completion of the folding of the longitudinal edge portions of the covering web is effected upon their passing over the oblique folding edges downstream from said break line.

As stated above, apparatus 20 constitutes means for C-folding a covering web about an article and securing longitudinal edge portions of the covering web to bottom surface regions of the article adjacent its longitudinal edges. As described, the means comprises first and second folding boards which are symmetrically configured about the longitudinal centerline of the apparatus, and which are serially arranged with respect to one another. Accordingly, the C-fold is symmetrical, and both edges are folding simultaneously. However, the apparatus may be configured to provide wraps wherein the edges of the covering web are overlapped. The edges of the covering web may be so overlapped by folding them serially about appropriately configured and serially arranged folding means: for example, placing the equivalent of the right longitudinal half of the apparatus upstream from an equivalent of the left longitudinal half of the apparatus. Indeed, such a wrap is more appropriately deemed an e-shape wrap. Additionally, only such an equivalent of one longitudinal half of the apparatus may be utilized to effect J-folding a covering web about one edge of an article.

While particular embodiments of the present invention have been illustrated and described, it would be obvious to those skilled in the art that various other changes and modifications can be made without departing from the spirit and scope of the invention. Accordingly, it is intended to cover in the appended claims all such changes and modifications that are within the scope of this invention.

What is claimed is:

1. An apparatus for longitudinally C-folding a running length of a flexible covering web about a longitudinally flexible article and for adhesively securing longitudinal edge portions of said flexible covering web to juxtaposed longitudinal edge regions of the bottom surface of said article, said apparatus comprising a transverse turning member, a first planar folding board having an upstream end disposed subjacent said turning member, a second planar folding board immediately downstream from said first folding board and pitched downwardly therefrom at a predetermined pitch angle, means for forwarding said article onto said first folding board, means for forwarding said covering web onto and about said turning member in a flat-out state so that its central span becomes juxtaposed said article as said article passes under said turning member, said first folding board having a nominal width about equal to or greater than the nominal width of said article, said second folding board having an oblique folding edge at each upstream corner thereof and which oblique folding edges are canted upstream at a predetermined acute angle with respect to the longitudinal center line of said second folding board, means for forwarding said article and said covering web together through said apparatus so that the longitudinal edge portions of said covering web are folded under the longitudinal edge regions of the bottom surface of said article and become juxtaposed therewith only upon passing over said oblique folding edges, said predetermined pitch angle being so related to said predetermined acute angle that all portions of said covering web traverse the same distance.

2. The apparatus of claim 1 wherein said means for forwarding said covering web causes the ultimate inside surface of said covering web to face upward prior to its being forwarded onto said turning member, and said apparatus further comprises means for gravitationally depositing a longitudinally extending bead of adhesive onto each longitudinal edge portion of said covering web, said adhesive comprising means for adhering said longitudinal edge portions of said covering web to said longitudinal edge regions of the bottom surface of said article as they become juxtaposed upon passing over said oblique folding edges.

3. The apparatus of claim 1 further comprising means for supporting said longitudinal edge portions of said covering web which are disposed outboard of the longitudinal side edges of said first folding board, and which longitudinal edge portions are being forwarded from said turning member to said oblique folding edges while obviating surface areas of said longitudinal edge portions from contacting other members of said apparatus.

4. The apparatus of claim 1 further comprising means for downwardly and inwardly effecting said C-folding without reverse folding said longitudinal edge portions.

5. The apparatus of claim 1 further comprising means for receiving and forwarding said article in the form of a running length of a core web.

6. The apparatus of claim 1 further comprising means for receiving and forwarding a stream of longitudinally spaced discrete said articles.

7. The apparatus of claim 1 further comprising means for securing a longitudinally extending strand of stretched elastic to each longitudinal edge portion of said covering web prior to juxtaposing the longitudinal edge portions of said covering web with said article.

* * * * *